United States Patent [19]

Ensminger

[11] 4,218,922
[45] Aug. 26, 1980

[54] ACOUSTIC INSPECTION OF SOLDER JOINTS
[75] Inventor: Dale Ensminger, Columbus, Ohio
[73] Assignee: Battelle Development Corporation, Columbus, Ohio
[21] Appl. No.: 943,447
[22] Filed: Sep. 18, 1978
[51] Int. Cl.³ .......................................... G01N 29/04
[52] U.S. Cl. .................................................. 73/588
[58] Field of Search .......................... 73/588, 582, 572
[56] References Cited
U.S. PATENT DOCUMENTS 3,106,838  10/1963  Crooks ..................................... 73/588
4,090,400  5/1978  Vahaviolos ............................... 73/582

FOREIGN PATENT DOCUMENTS 2213154  9/1972  Fed. Rep. of Germany ............. 73/588

*Primary Examiner*—Anthony V. Ciarlante
*Attorney, Agent, or Firm*—Barry S. Bissell

[57] ABSTRACT

A method for flaw detection in solder joints, especially on printed circuit (PC) boards, by means of the application of sonic and ultrasonic energy, with or without an electrical current therewith, upstream of the solder joint and comparison of these acoustic and electrical inputs to their respective modulated outputs downstream of the joint.

3 Claims, 3 Drawing Figures

ACOUSTIC INSPECTION OF SOLDER JOINTS

BACKGROUND OF THE INVENTION

Solder joints between lead wires and terminal conductor pads or between two wires may temporarily provide good electrical conduction but lack the mechanical strength to survive physical shock and fatigue in their intended use. For example, discrete elements on printed circuit boards may initially have a continuous electrical contact through a solder joint to the printed conductor, but when used in mobile systems may be subject to vibration causing cracks or physical discontinuities in the solder joint resulting in a current interruption. Therefore, electrical, quality-control testing would be insufficient to detect physical defects in the solder joint which may cause the joint to fail in use. Such defects might be related to poor adherence of the solder and wire, inclusions, porosity, cold solder, a break or other similar flaws.

Commonly available ultrasonic flaw detectors apply an acoustic wave to a material and monitor and receive an echo from the flaw (usually an inclusion or crack).

SUMMARY OF THE INVENTION

It is an object of the present invention to provide a non-destructive flaw detection method for solder joints.

It is also an object to provide such a method which is rapid, reliable and which can be automated, especially in the inspection of printed circuit boards.

In accordance with the objective, the invention is an acoustic inspection method for physical defects in soler bonds. The method for qualitative inspection of a solder joint between a lead wire and a conductor comprises applying a known acoustic wave to the lead wire such that the wave is transmitted to the solder joint, modulated by the solder bond and (if the bond is not completely broken) passed through to the conductor; monitoring and receiving the modulated acoustic wave from the conductor; and, comparing the modulated wave received from the conductor with the applied wave in the lead wire and to known modulations in acoustic waves caused by specific defects in solder bonds, whereby to detect the modulations of the applied wave which are characteristic of unacceptable solder bonds.

An alternative to the above method comprises applying the acoustic wave and an electrical current to the lead wire, monitoring and receiving the modulated electrical current from the conductor; and, comparing the modulated current output with the applied current and with known modulations of electrical current caused by specific defects in solder bonds whereby to detect the current modulations which are characteristic of unacceptable solder bonds.

Typically an oscilloscope is used to observe both the applied acoustical or electrical energy and the modulated outputs from the conductor. Other digital or analog meters may be used, for example, an ammeter or voltmeter may be used to observe the modulated current in the alternative embodiment.

The acoustic transducers may typically use piezoelectric materials, but may also utilize magnetostrictive or magnetic materials. The frequency range of operation appears not to be critical but, for convenience, is preferably about 60 hz to 200 khz. The acoustic wave is preferably in the ultrasonic range of about 20-200 khz.

The method is amenable to automation wherein the applied acoustic wave and the modulated wave output may be compared by a machine system which makes decisions based on programmed limits and deviations in amplitude, frequency, phase or other variables in the acoustic wave.

DETAILED DESCRIPTION OF THE INVENTION

Figure 1:
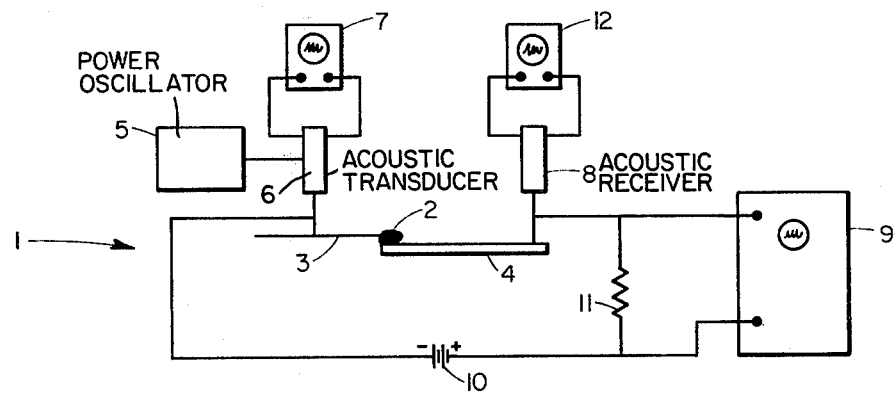
FIG. 1 is a schematic of the testing apparatus.

FIG. 1 is a schematic drawing of the apparatus used in practicing the invention. The inspection system 1 is able to apply an ultrasonic or sonic wave with or without an electrical current to the leadwire 3 and the solder joint 2 and to receive both the modulated acoustic wave and modulated current from the conductor 4. The solder joint connects the lead wire 3 to the conductor 4 which can be a conductive strip on a substrate or printed circuit board or it can be a second wire. The lead wire 3 and conductor 4 form part of a closed loop also comprising current source 10, acoustic transducer and probe 6, acoustic receiver and probe 8, a resistor 11 and an output indicator 9 across the resistor 11.

The current source is shown as a battery but could be any constant, AC or DC, low-voltage (in the range of 2–30 v) power supply. A power supply of 2 volts and a 10 ohm, ½ watt resistor 11 may be used, for example. The choice of voltage and resistance may be chosen to provide a signal in a convenient range to the output indicator 9.

The output indicator may be used to examine transducer voltage and current characteristics and phase relationships therebetween, modulated acoustical signals, or modulated current indications. For visual inspection, an oscilloscope 9 (as shown) is preferred, whereas for automatic inspection, strip chart recorders, tapes or other graphic records are preferred from which an automated machine system could be used to identify unacceptable solder bonds.

Acoustic transducer and probe 6 is used to apply an acoustic wave to the solder joint and may be piezoelectric, magnetostrictive or electromagnetic. These are preferably used for inspection at high, intermediate and low frequencies respectively. The invention may be used over a wide range of frequencies, especially depending on the type and sensitivity of the solder joint. Miniturized, sensitive joints may dictate the use of frequencies in the 1 Mhz range whereas ordinary, heavier-wire solder joints may dictate the use of from about 60 hz to 200 khz. A 28 khz transducer was used in the course of experimenting with the invention.

The transducer impedance should be such that the load impedance produces a measurable effect in the transducer circuit if the user desires to use the reflected impedance as a benchmark of the applied wave for purposes of comparison with the modulated wave in the conductor. The transducer position and contact with the lead wire may be controlled manually or automatically with a spring load, for example, giving uniform pressure contact with successive solder joints being tested.

The acoustic transducer 6 is driven by an acoustic power oscillator 5. This can be a tube type or transistor power oscillator.

An input indicator 7 is associated with the acoustic transducer and the power oscillator for observing the input acoustic wave. The indicator may be responsive to reflected load impedance, shown by the plate current in a tube type power oscillator, or may identify the current from a voltage power supply, or frequency or voltage across the transducer. The indicator may be an oscilloscope (as shown) or a meter, tape, strip chart recorder, etc.

Acoustic receiver and probe 8 is a broad-band contact type transducer and is monitored by an output indicator 12, shown as an oscilloscope. The transducer may be preferably piezoelectric or condenser type. The acoustic receiver picks up the modulated acoustic wave from the conductor after it has passed through the solder joint. The output of the acoustic receiver is then displayed or recorded in the output indicator 12 or may be fed to a data processing unit for automated operation.

The system described above may perform two alternative tests to effect the inspection. The first test of the soundness of a solder joint is the degree of conduction of the acoustic wave across the joint. The second test is the degree of conduction of electrical current across an acoustically stimulated solder joint. The former test does not require the elements of the system which relate only to the creation of a current across the solder joint. The latter test requires the apparatus as described and the simultaneous passage of an acoustic carrier and electrical current across the solder joint.

Figure 2:
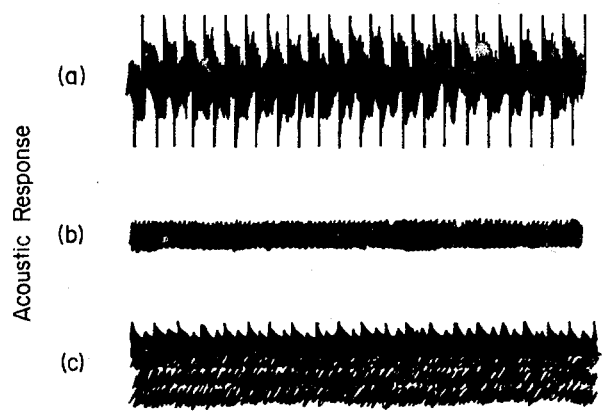
FIG. 2 is a representation of an oscilloscope trace of the acoustic output of the test.

In the acoustic conduction test, the acoustic energy is conducted through the solder joint in a manner that depends on the conditions within and surrounding the solder joint. If the acoustic transducer is brought into contact with the lead wire, an acoustic wave such as shown in FIG. 2(a) is applied to the joint. If the solder joint has good bonding the acoustic wave will be received by the acoustic receiver from the conductor without a great deal of modulation. The output will essentially duplicate the applied wave shown in FIG. 2(a) with only minor attentuation in amplitude. On the contrary, inclusions or porosity in the solder joint, which result in an unacceptable bond, interfere with optimum energy transfer and severely modulate the applied wave, particularly in attenuating the amplitude of the wave, such as shown in FIG. 2(b). A completely separated junction will transmit no sound but some energy may bypass the junction through the surrounding media. An open junction or broken lead may cause chatter (noise) which modulates the applied wave to an output wave such as shown in FIG. 2(c).

Figure 3:
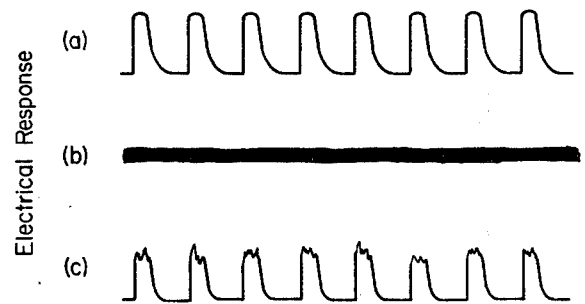
FIG. 3 is a representation of an oscilloscope trace of the electrical output of the test.

In the alternative, employing the electrical current in addition to the acoustic wave, a direct current is applied through the acoustic transducer. The transducer thereby acts as a rapid switching device, opening and closing the current path through the probe to the lead wire, and resulting in a pulsed current condition in the lead wire such as represented in FIG. 3(a) (the peak height being the voltage drop across the resistor 11). A good solder joint would pass the applied current in substantially unmodulated form so that the voltage indicator 9 across the circuit resistor 11 would essentially reproduce the applied wave. However, should severe inclusions or porosity occur in the solder joint the output (modulated) current would produce a voltage drop resembling FIG. 3(b) wherein the amplitude of the voltage drop is depressed by the inclusions down to a zero drop when no current flows across a discontinuous joint. A cracked joint would result more in a pattern shown in FIG. 3(c) wherein some current periodically passes the joint but may be modulated significantly in phase, or amplitude due to the combined switching effects of the transducer and the cracked joint.

DESCRIPTION OF THE PREFERRED EMBODIMENTS

Example 1—Acoustic Transmission

Sample solder joints were prepared by bonding copper wires to conductors (nails). Joint 1 was designed to be a good joint, joint 2 was designed to contain inclusions of masking tape, and joint 3 was designed to simulate a broken bond or "cold-solder" joint by moving the lead slightly while soldering and cooling. The ends of the wire leads and conductor were restrained by attachment to a board and a small steel probe activated by a handheld piezoelectric transducer at 28 khz was brought into contact with each of the lead wires. The ultrasonic wave was transmitted through the joints and detected by a piezoelectric contact probe. The applied or input ultrasonic wave and the output modulated waves were monitored with multiple sweep oscilloscopes. FIG. 2(a) is a representation of both the applied wave and the output wave through the good joint 1. FIG. 2(b) shows the oscilloscope representation of the modulated output wave through joint 2 having significant inclusions. The attenuation of the applied wave due to the poor bond is apparent. FIG. 2(c) likewise represents the modulation and noise of the applied wave through joint 3 due to the broken or cold-solder bond. The noise caused by the joint nearly envelopes the applied wave.

Example 2—Electrical Transmission

The same three solder joints of Example 1 were used in the alternative inspection method. The apparatus was the same as in Example 1 including the elements for supplying an electrical current all as shown in FIG. 1. The ultrasonic transducer and probe were used as the electrode to supply current from the current source to the solder joints as well as the ultrasound. The receiving electrode on the conductor consisted of a slender, needle-shaped bar and was electrically connected with the resistor, the current source and the output indicator as shown in FIG. 1.

A potential of 2 volts was provided by the current source and the ultrasound of high amplitude was applied at 28 khz. FIG. 3(a) is a representation of the oscilloscope display of the applied current and of the output current through the good joint 1 as measured by the voltage drop across the resistor. The ultrasonic transducer operates as a switch to essentially provide a high amplitude pulsed current to the joint.

FIG. 3(b) and 3(c) are representations of the oscilloscope display of the voltage drop across the resistor caused by the modulated output current through joints 2 and 3, respectively. The effects of the significant inclusions in joint 2 is a complete electrical discontinuity. The effect of the broken or cold-solder joint 3 is a chattering of the broken joint resulting in intermittant opening and closing of the circuit through the joint. This intermittant switching is superimposed on the periodic switching of the ultrasonic transducer. This results in an output showing switching in periodic clusters. The periodicity in FIG. 3(a) is indicative of maximum d.c. voltage (2 volts) followed by decay to zero voltage due to the ultrasonic transducer switching. However, FIG. 3(c) shows that contact of broken segments in the solder joint are only instantaneous so that sustained d.c. peak voltage may not be reached before elimination of contact, breaking the circuit.

The comparison of the applied acoustic wave or current with the modulated output and the decision of acceptability of the solder bond based on the magnitude of the modulation by the solder bond conditions is arbitrary to some extent. The very good and the very poor bonds are easily identified in the output but the marginal solder bonds will produce some relative modulation. To develop a degree of modulation, determinable manually or by a machine system, which can serve as the dividing line between acceptable and unacceptable bonds should involve a simulation whereby solder joints producing a wide range of results in the inventive inspection method are life tested. A dividing line can then be made at the degree of modulation which corresponds to the results obtained for the acceptable solder joints in the simulation, having regard for the probabilities of achieving a desired life. Comparison of acoustic response may preferably be based on the amplitude of the waves and the amount of generated noise. Comparison of electrical response may preferably be based on the amplitude and the continuity of the waves. Other indications may be equally as useful after routine experimentation and experience with the test equipment.

I claim:

1. A method for qualitatively inspecting the integrity of a solder bond joining a lead wire and a conductor which comprises
   (A) applying an acoustic wave to the solder joint,
   (B) applying a known current to the lead wire such that the current is carried through the solder bond to the conductor,
   (C) receiving from the conductor the current as modulated by conditions in the acoustically stimulated solder bond, and
   (D) comparing the modulated current received from the conductor to the applied current in the lead wire whereby to detect the modulations of the applied current which are characteristic of unacceptable solder bonds.

2. The method of claim 1 wherein a direct current is applied to an acoustic transducer which then applies both the acoustic wave and the current to the lead wire and the solder joint.

3. The method of claim 1 wherein the modulated current from the solder bond is received from the conductor by passing the current from the conductor through a resistor and detecting the voltage drop there across.

* * * * *